US012600972B2

(12) United States Patent
Jiang

(10) Patent No.: US 12,600,972 B2
(45) Date of Patent: Apr. 14, 2026

(54) LIPOPOLYSACCHARIDE (LPS) APTAMERS AND ASSOCIATED METHODS

(71) Applicant: Fresenius Medical Care Holdings, Inc., Waltham, MA (US)

(72) Inventor: Tao Jiang, Knoxville, TN (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 1109 days.

(21) Appl. No.: 17/591,485

(22) Filed: Feb. 2, 2022

(65) Prior Publication Data

US 2022/0243206 A1 Aug. 4, 2022

Related U.S. Application Data

(60) Provisional application No. 63/145,625, filed on Feb. 4, 2021.

(51) Int. Cl.
*C12N 15/115* (2010.01)
*C12Q 1/689* (2018.01)

(52) U.S. Cl.
CPC ............ *C12N 15/115* (2013.01); *C12Q 1/689* (2013.01); *C12N 2310/16* (2013.01); *C12N 2310/531* (2013.01)

(58) Field of Classification Search
CPC .............. C12N 15/115; C12N 2310/16; G01N 2400/50
See application file for complete search history.

(56) References Cited

U.S. PATENT DOCUMENTS

| | | | |
|---|---|---|---|
| 7,906,280 B2 | 3/2011 | Bruno et al. | |
| 11,970,698 B2 * | 4/2024 | Jiang ................... | C12N 15/115 |
| 2009/0186342 A1 | 7/2009 | Bruno et al. | |
| 2011/0065086 A1 | 3/2011 | Bruno | |
| 2012/0071639 A1 | 3/2012 | Bruno | |
| 2014/0287424 A1 | 9/2014 | Cho et al. | |
| 2019/0257831 A1 | 8/2019 | Rabe Ralam et al. | |
| 2020/0249228 A1 | 8/2020 | Jiang et al. | |

FOREIGN PATENT DOCUMENTS

| | | |
|---|---|---|
| CN | 108982623 A | 12/2018 |
| CN | 109270259 A | 1/2019 |
| CN | 110082524 A | 8/2019 |
| CN | 110274948 A | 9/2019 |
| CN | 110609071 A | 12/2019 |
| CN | 106834295 B | 4/2020 |
| KR | 10-2012-0116224 A | 10/2012 |
| KR | 10-2014-0011086 A | 1/2014 |
| WO | 2020/152111 A1 | 7/2020 |
| WO | 2020/227736 A2 | 11/2020 |

OTHER PUBLICATIONS

Ye, Hua, et al. "Fluorometric determination of lipopolysaccharides via changes of the graphene oxide-enhanced fluorescence polarization caused by truncated aptamers." Microchimica Acta 186 (2019): 1-8. (Year: 2019).*

Davydova, Anna, et al. "Aptamers against pathogenic microorganisms." Critical reviews in microbiology 42.6 (2016): 847-865. (Year : 2016).*

Bruno et al. "In vitro antibacterial effects ofantilipopolysaccharide DNA aptamer-C1qrscomplexes" Folia Microbiologica, vol. 53, No. 4 , Aug. 31, 2008, pp. 295-302.

Ding et al. Single-Stranded DNA Oligoaptamers: Molecular Recognition and LPS Antagonism Are Length- and Secondary Structure-Dependent, Journal of Innate Immunity, vol. 1, No. 1 , Jul. 2008, pp. 46-58.

Ellington et al. "In vitro selection of RNA molecules that bind specific ligands" Nature (Aug. 1990) 346(6287) pp. 818-822.

Gold et al. "Aptamers and the RNA world, past and present." Cold Spring Harb. Perspect. Biol. (Mar. 2012) 4(3), a003582.

International Search Report for International Application No. PCT/US2022/014964, mailed Jul. 11, 2022, 11 pages.

International Written Opinion for International Application No. PCT/US2022/014964, mailed Jul. 11, 2022, 12 pages.

Kim et al. "Harnessing aptamers for electrochemical detection of endotoxin" Analytical Biochemistry, vol. 424, No. 1, Feb. 25, 2012, pp. 12-20.

Li et al: "Advances in detection of infectious agents by aptamer-based technologies" Emerging Microbes & Infections, vol. 9 , No. 1 , Jul. 20, 2020, pp. 1671-1681.

Schütze et al. "Probing the SELEX Process with Next-Generation Sequencing" PLoS One 6(12): e29604 (Dec. 2011). DOI: 10.1371/journal.pone.0029604.

Su et al. "Determination of endotoxin through an aptamer-based impedance biosensor" Biosensors and Bioelectronics, vol. 32, No. 1 (Dec. 2011) 32-36.

Tuerk et al. "Systematic evolution of ligands by exponential enrichment: RNA ligands to bacteriophage t4 DNA polymerase." Science (Aug. 1990) vol. 249, Issue 4968, pp. 505-510.

Wang et al. "Particle Display: A Quantitative Screening Method for Generating High-Affinity Aptamers" Angewandte Communications International Edition 53(19): pp. 4796-4801 (May 2014). DOI: 10.1002/anie.201309334.

Wen et al: "A novel lipopolysaccharide-antagonizing aptamer 17-20 protects mice against endotoxemia" Biochemical and Biophysical Research Communications, vol. 382, Issue 1, Apr. 24, 2009, pp. 140-144.

Zhang "Synthesis of peptidoglycan peptides for DNA aptamer selection" (T). University of British Columbia (Oct. 2018). Retrieved from open.library.ubc.ca/collections/ubctheses/24/items/1.0372791.

Zhu et al. "Colorimetric detection and typing of E. coli lipopolysaccharides based on a dual aptamer-functionalized gold nanoparticle probe" Mxcrochimica Acta, Springer Vienna, vol. 186, No. 2 , Jan. 14, 2019.

Zhuo et al. "Recent Advances in SELEX Technology and Aptamer Applications in Biomedicine" Int. J. Mol. Sci. (Oct. 2017) 18(10), 2142; doi:10.3390/ijms18102142.

(Continued)

*Primary Examiner* — Abigail Vanhorn

(74) *Attorney, Agent, or Firm* — TraskBritt

(57) ABSTRACT

Described are a number of aptamers that are specific to bind with lipopolysaccharide (LPS), and associated methods.

22 Claims, 2 Drawing Sheets

Specification includes a Sequence Listing.

(56)            References Cited

OTHER PUBLICATIONS

ZUKER "Mfold web server for nucleic acid folding and hybridization prediction." Nucleic Acids Res. vol. 31, Issue 13, pp. 3406-3415 (Jul. 2003).

* cited by examiner

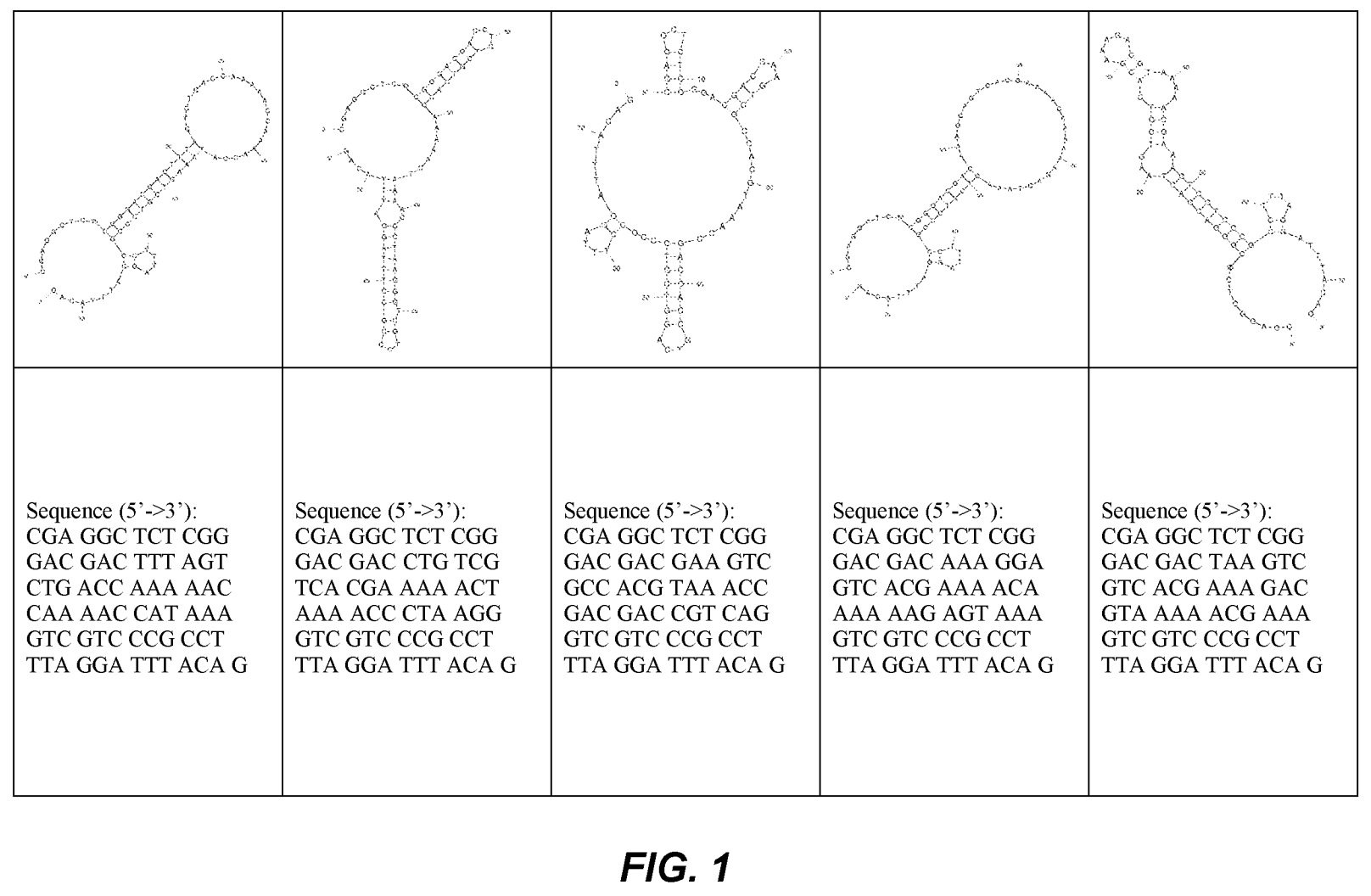

Sequence (5'->3'):
CGA GGC TCT CGG
GAC GAC TAA GTC
GTC ACG AAA GAC
GTA AAA ACG AAA
GTC GTC CCG CCT
TTA GGA TTT ACA G Sequence (5'->3'):
CGA GGC TCT CGG
GAC GAC AAA GGA
GTC ACG AAA ACA
AAA AAG AGT AAA
GTC GTC CCG CCT
TTA GGA TTT ACA G Sequence (5'->3'):
CGA GGC TCT CGG
GAC GAC GAA GTC
GCC ACG TAA ACC
GAC GAC CGT CAG
GTC GTC CCG CCT
TTA GGA TTT ACA G Sequence (5'->3'):
CGA GGC TCT CGG
GAC GAC CTG TCG
TCA CGA AAA ACT
AAA ACC CTA AGG
GTC GTC CCG CCT
TTA GGA TTT ACA G Sequence (5'->3'):
CGA GGC TCT CGG
GAC GAC TTT AGT
CTG ACC AAA AAC
CAA AAC CAT AAA
GTC GTC CCG CCT
TTA GGA TTT ACA G

FIG. 1

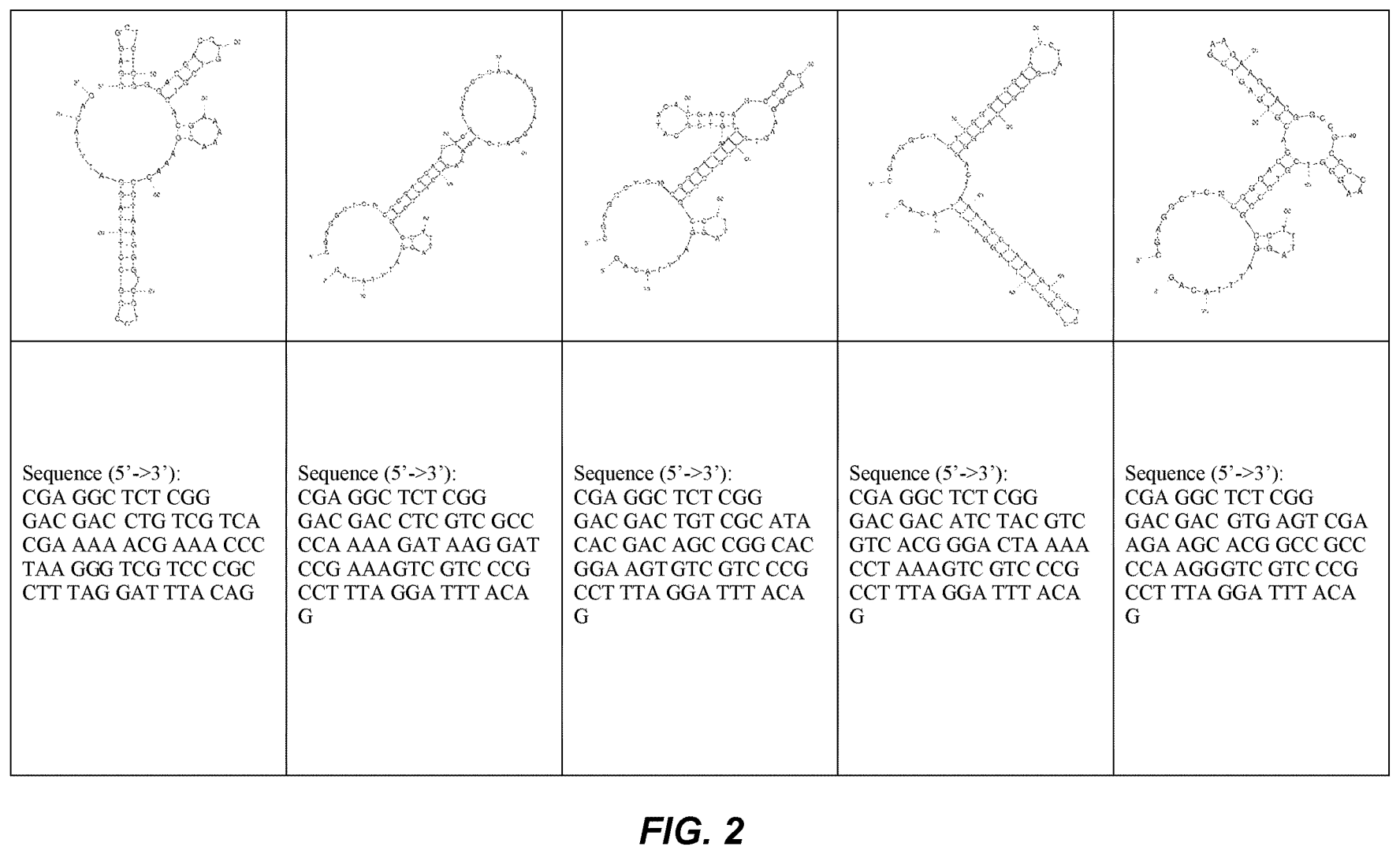

Sequence (5'->3'):
CGA GGC TCT CGG
GAC GAC GTG AGT CGA
AGA AGC ACG GCC GCC
CCA AGGGTC GTC CCG
CCT TTA GGA TTT ACA
G Sequence (5'->3'):
CGA GGC TCT CGG
GAC GAC ATC TAC GTC
GTC ACG GGA CTA AAA
CCT AAAGTC GTC CCG
CCT TTA GGA TTT ACA
G Sequence (5'->3'):
CGA GGC TCT CGG
GAC GAC TGT CGC ATA
CAC GAC AGC CGG CAC
GGA AGT GTC GTC CCG
CCT TTA GGA TTT ACA
G Sequence (5'->3'):
CGA GGC TCT CGG
GAC GAC CTC GTC GCC
CCA AAA GAT AAG GAT
CCG AAAGTC GTC CCG
CCT TTA GGA TTT ACA
G Sequence (5'->3'):
CGA GGC TCT CGG
GAC GAC CTG TCG TCA
CGA AAA ACG AAA CCC
TAA GGG TCG TCC CGC
CTT TAG GAT TTA CAG

*FIG. 2*

LIPOPOLYSACCHARIDE (LPS) APTAMERS AND ASSOCIATED METHODS

CROSS-REFERENCE TO RELATED APPLICATION

This application claims the benefit under 35 U.S.C. § 119(e) of U.S. Provisional Patent Application Ser. No. 63/145,625, filed Feb. 4, 2021, the disclosure of which is hereby incorporated herein in its entirety by this reference.

TECHNICAL FIELD

This application relates generally to biochemistry, and more particularly to aptamers that specifically bind to lipopolysaccharides ("LPS") and associated methods.

STATEMENT ACCORDING TO 37 C.F.R. § 1.821(c) or (e)—SEQUENCE LISTING SUBMITTED AS A TXT AND PDF FILES

Pursuant to 37 C.F.R. § 1.821(c) or (e), files containing a TXT version and a PDF version of the Sequence Listing have been submitted concomitant with this application, the contents of which are hereby incorporated by reference.

BACKGROUND

Lipopolysaccharides ("LPS" or "endotoxins") are large molecules consisting of a lipid and a polysaccharide composed of O-antigen, outer core, and inner core joined by a covalent bond, which are found in the outer membrane of Gram-negative bacteria.

Aptamers are short strands of oligonucleotides that form a three-dimensional structure able to bind a target material with high affinity and specificity. Aptamers can, for example, be used as elements of biosensors that can recognize molecules in detection and analysis systems, similar to antibodies.

Oligonucleotide-based aptamers have several advantages over protein-based antibodies. First, the aptamer can be synthesized in vitro, second, various organic and inorganic materials including toxins can be used as aptamer targets, and third, aptamers are more stable at various temperatures than protein antibodies.

Once aptamers have been identified and obtained, they can be reproduced with relatively low cost and high batch-consistency by automated oligomer synthesis. Further, aptamers can relatively easily be modified to introduce useful functional groups, such as fluorescent molecules or photoreactive groups.

Aptamers directed against LPS have been referred to in the art. See, e.g., US 2012071639 A1 (DNA ligand), KR20140011086 A (RNA aptamer), US2019257831 A1 (biosensor), CN 109270259 A (method for detecting endotoxin using undisclosed aptamer), CN 110082524 A (method for detecting endotoxin using undisclosed aptamer), CN110274948 A (biosensor for detecting endotoxin using undisclosed aptamer), CN110609071 A (method for detecting endotoxin using aptamer), U.S. Pat. No. 7,906,280 (Mar. 15, 2011) (methods of producing interachain fluorophore-quencher fret-aptamers and assays), US 2011065086 A (methods of producing homogeneous plastic-adherent aptamer-magnetic bead-fluorophore and other sandwich assays), KR20120116224 A (a sensor for lipopolysaccharide sensing and preparation method thereof), US2014287424 A (slide chip for detection sensor of food-borne pathogens and preparation method thereof), and WO 20152111 A1 (aptamer and use of the aptamer in the diagnosis and treatment of cancer), the contents of each of which are incorporated herein by this reference in its entirety.

SUMMARY OF THE DISCLOSURE

Described herein are particularly useful DNA aptamers to LPS.

In certain embodiments, such an aptamer has a loop structure. In certain embodiments, such an aptamer has a double-stranded stem structure. In certain embodiments, such an aptamer further comprises at least one labeling substance such as an optical label, an electrochemical label, a radioisotope, or a combination thereof.

Specifically described are the exemplary DNA aptamers of SEQ ID NOs: 1-10.

```
(5'->3') (SEQ ID NO: 1):
CGA GGC TCT CGG GAC GAC TTT AGT CTG ACC AAA AAC

CAA AAC CAT AAA GTC GTC CCG CCT TTA GGA TTT ACA G;

(5'->3') (SEQ ID NO: 2):
CGA GGC TCT CGG GAC GAC CTG TCG TCA CGA AAA ACT

AAA ACC CTA AGG GTC GTC CCG CCT TTA GGA TTT ACA G;

(5'->3') (SEQ ID NO: 3):
CGA GGC TCT CGG GAC GAC GAA GTC GCC ACG TAA ACC

GAC GAC CGT CAG GTC GTC CCG CCT TTA GGA TTT ACA G;

(5'->3') (SEQ ID NO: 4):
CGA GGC TCT CGG GAC GAC AAA GGA GTC ACG AAA ACA

AAA AAG AGT AAA GTC GTC CCG CCT TTA GGA TTT ACA G;

(5'->3') (SEQ ID NO: 5):
CGA GGC TCT CGG GAC GAC TAA GTC GTC ACG AAA GAC

GTA AAA ACG AAA GTC GTC CCG CCT TTA GGA TTT ACA G;

(5'->3') (SEQ ID NO: 6):
CGA GGC TCT CGG GAC GAC CTG TCG TCA CGA AAA ACG

AAA CCC TAA GGG TCG TCC CGC CTT TAG GAT TTA CAG;

(5'->3'): (SEQ ID NO 7):
CGA GGC TCT CGG GAC GAC CTC GTC GCC CCA AAA GAT

AAG GAT CCG AAA GTC GTC CCG CCT TTA GGA TTT ACA G;

(5'->3') (SEQ ID NO: 8):
CGA GGC TCT CGG GAC GAC TGT CGC ATA CAC GAC AGC

CGG CAC GGA AGT GTC GTC CCG CCT TTA GGA TTT ACA G;

(5'->3') (SEQ ID NO: 9):
CGA GGC TCT CGG GAC GAC ATC TAC GTC GTC ACG GGA

CTA AAA CCT AAA GTC GTC CCG CCT TTA GGA TTT ACA G;
and (5'->3') (SEQ ID NO: 10):
CGA GGC TCT CGG GAC GAC GTG AGT CGA AGA AGC ACG

GCC GCC CCA AGG GTC GTC CCG CCT TTA GGA TTT ACA G.
```

As can be seen, the "core sequences" of these aptamers are, respectively, SEQ ID NOs: 11-20:

```
(SEQ ID NO: 11):
TTT AGT CTG ACC AAA AAC CAA AAC CAT AAA;
```

-continued
```
(SEQ ID NO: 12):
CTG TCG TCA CGA AAA ACT AAA ACC CTA AGG;

(SEQ ID NO: 13):
GAA GTC GCC ACG TAA ACC GAC GAC CGT CAG;

(SEQ ID NO: 14):
AAA GGA GTC ACG AAA ACA AAA AAG AGT AAA;

(SEQ ID NO: 15):
TAA GTC GTC ACG AAA GAC GTA AAA ACG AAA;

(SEQ ID NO: 16):
CTG TCG TCA CGA AAA ACG AAA CCC TAA GG;

(SEQ ID NO: 17):
CTC GTC GCC CCA AAA GAT AAG GAT CCG AAA;

(SEQ ID NO: 18):
TGT CGC ATA CAC GAC AGC CGG CAC GGA AGT;

(SEQ ID NO: 19):
ATC TAC GTC GTC ACG GGA CTA AAA CCT AAA;
and (SEQ ID NO: 20):
GTG AGT CGA AGA AGC ACG GCC GCC CCA AGG.
```

In certain embodiments, the DNA aptamer core sequence includes:

```
                                 (SEQ ID NO: 21)
     GTC GTC ACG AAA RVH VAA AAV MBB AAA
``` wherein A, C, G, and T have their customary meanings, wherein R is A or G; wherein V is A, C, or G; wherein B is C, G, or T; wherein H is A, C, or T; and wherein M is A or C.

The aptamers of SEQ ID NOs: 1-10 also include PCR primer annealing regions (or "primer sequences") (5'-CGA GGC TCT CGG GAC GAC (SEQ ID NO:22)—[core sequence]—GTC GTC CCG CCT TTA GGA TTT ACA G-3' (SEQ ID NO:23)), although other PCR primer annealing regions may be used so long as they do not interfere with the binding of the aptamer to LPS.

Thus, described is a DNA aptamer comprising a polynucleotide of any of the following (a) to (c) and capable of binding to lipopolysaccharides ("LPS"): (a) a polynucleotide comprising a core sequence set forth in any one of SEQ ID NOs: 11-21, (b) a polynucleotide comprising a core sequence having the deletion, substitution, insertion and/or addition of one to two bases in the core sequence set forth in any one of SEQ ID NOs: 11-21, and (c) a polynucleotide comprising a core sequence having a sequence identity of 90% or more to the core sequence set forth in any one of SEQ ID NOs: 11-21.

In certain embodiments, provided is a method for detecting LPS, including binding an aptamer as described herein to LPS to thereby detect the LPS.

Thus, further described herein are the DNA aptamers and their use for detecting LPS.

BRIEF DESCRIPTION OF THE DRAWINGS

FIG. 1 shows the predicted secondary structures of the DNA aptamers of SEQ ID NOs: 1-5 (from left to right, respectively).

FIG. 2 shows the predicted secondary structures of the DNA aptamers of SEQ ID NOs: 6-10 (from left to right, respectively).

DETAILED DESCRIPTION

The term "base pairing," as used herein, refers to base pairing formed of a pair of complementary synthetic bases, such as adenine and thymine or guanine and cytosine.

The term "DNA aptamer," as used herein, refers to an aptamer sequence composed of DNA nucleotides. A DNA aptamer is a ligand molecule that firmly and specifically binds to a target molecule through a conformational structure formed based upon a secondary and a tertiary structure of a single-stranded nucleic acid molecule via hydrogen bonding or other interactions.

The term "target molecule," as used herein, refers to a substance to which the DNA aptamer can bind. For instance, a target molecule is LPS.

In one aspect, described is an agent for detecting LPS, the agent comprising the DNA aptamer as described herein. In certain embodiments, the agent for detecting LPS is an agent that is used for detecting LPS in vitro utilizing the ability of a described DNA aptamer to bind to LPS. For example, the DNA aptamer is labeled with a fluorescence reagent beforehand, and the labeled DNA aptamer is admixed with a sample.

In one aspect, described is a composition for detecting LPS, the composition comprising a DNA aptamer as described herein.

In principle, the composition may be prepared in accordance with a method known in the art. For example, see the method described in Remington's Pharmaceutical Sciences (Merck Publishing Co., Easton, Pa.).

For example, preparations can be prepared by a method generally used in the art, comprising dissolving at least one DNA aptamer hereof in, for example, a pharmaceutically acceptable solvent and adding, for example, a pharmaceutically acceptable carrier thereto, if needed.

Examples of "pharmaceutically acceptable solvent(s)" include water, ethanol, propylene glycol, ethoxylated isostearyl alcohol, polyoxylated isostearyl alcohol, and a polyoxyethylene sorbitan fatty acid ester.

In one aspect, the disclosure relates to a kit for detecting LPS or for more generally detecting Gram negative bacteria in a sample, the kit comprising the DNA aptamer as described herein. In addition to the DNA aptamer as described herein, the kit as described herein may comprise, for example, a buffer, a label reagent, and/or instructions.

In certain embodiments, the aptamer is labeled with a labeling substance, and detection of the LPS may occur by detecting the labeling substance. Examples of labeling substances include a dye, a fluorescent dye, a radioisotope, an antibody, an antigen, and an enzyme. Examples of the fluorescent dye include FITC. Such labels may be attached to a specific base or a specific structure of the aptamer, for example, a specific site of a hairpin-loop structure or a 3' or 5' terminus of an aptamer.

An optical label may be exemplified by a fluorescent material. For example, the fluorescent material may be selected from among fluorescein, 6-FAM, rhodamine, Texas Red, tetramethyl rhodamine, carboxyl rhodamine, carboxyl rhodamine 6G, carboxyl rhodol, carboxyl rhodamine 110, Cascade Blue, Cascade Yellow, coumarin, Cy2 (cyanine 2), Cy3, Cy3.5, Cy5, Cy5.5, Cy-chromium, phycoerythrin, PerCP (peridinin chlorophyll—a protein), PerCP-Cy5.5, JOE (6-carboxy-4',5'-dichloro-2',7'-dimethoxyfluorescin), NED, ROX (5-(and-6)-carboxy-X-rhodamine), HEX, Lucifer Yellow, Marina Blue, Oregon Green 488, Oregon Green 500, Oregon Green 514, Alexa Fluor, 7-amino-4-methylcoumarin-3-acetic acid, BODIPY FL, BODIPY FL-Br 2, BODIPY 530/550, conjugations thereof, and combinations thereof.

The optical label may be an enzyme suitable for use in enzyme-linked immunosorbent assay ("ELISA"). The enzyme used for ELISA may include alkaline phosphatase, horseradish peroxidase, luciferase, or glucose oxidase. When the enzyme is used as the optical label, a chemiluminescent material may be employed in order to induce a chemiluminescent reaction, the chemiluminescent material being selected from among luminol, isoluminol, luciferin, lucigenin, 3-(2'-spiroadamantane)-4-methoxy-4-(3"-phosphoryloxy)phenyl-1,2-dioxetan-e (AMPPD), and disodium 3-(4-methoxyspiro {1,2-dioxetane-3,2'-(5'-chloro)tricyclo [3.3.1.13,7]decan}-4-yl)phenyl phosphate (CSPD). In addition thereto, any material appropriately selected by those skilled in the art is useful.

An optical label may be a fluorescence resonance energy transfer ("FRET") pair, which includes a donor fluorophore and an acceptor fluorophore spaced apart from each other by an appropriate distance and in which the fluorescence emission of the donor is suppressed or quenched by the acceptor. The donor fluorophore may include FAM, TAMRA, VIC, JOE, Cy3, Cy5 and Texas Red. The acceptor fluorophore may be selected so as to overlap its excitation spectrum with the emission spectrum of the donor. The acceptor may be a non-fluorescence acceptor for quenching a wide range of donor.

Also described herein is an aptamer-immobilized carrier in which the aptamer for detecting LPS (or a multi-structure aptamer thereof) is immobilized on the surface of a solid phase carrier. As the solid phase carrier, it is possible to employ carriers of various shapes such as sheet-like, plate-like, cylindrical, and spherical carriers. As the material for a carrier, a plastic, metal, glass, or the like may be used. Typically, any material may be used so long as it is a material able to have an aptamer immobilized thereto, for example for use with a lateral flow assay device. (See, e.g., U.S. Patent Application Publication 20200249228 A1 to Jiang et al. (Aug. 6, 2020) for "Rapid Diagnosis of Peritonitis in Peritoneal Dialysis Patients," the contents of which are incorporated herein by this reference.) For example, an aptamer-immobilized carrier may be a carrier in which the aptamer is immobilized on the surface of a sheet-like solid phase carrier.

The invention is further described with the aid of the following illustrative Examples.

EXAMPLES

Example I

After screening a nucleic acid library over several generations against the target lipopolysaccharides (LPS) for specificity over counter-target lipoteichoic acid (LTA), the enriched library was processed to identify aptamer candidates. Libraries produced by initial screening were sequenced for used in the differential analysis and identification of the most promising aptamer sequences in terms of binding performance. These candidates were qualitatively assessed for response to LPS in 1×SELEX buffer before the best candidates were characterized.

As will be appreciated by those of skill in the art, SELEX begins with the synthesis of a very large oligonucleotide library consisting of randomly generated sequences of fixed length flanked by constant 5' and 3' ends that serve as primers. For a randomly generated region of length n, the number of possible sequences in the library is 4n (n positions with four possibilities (A, T, C, or G) at each position). The sequences in the library are exposed to the target ligand—which may be a protein or a small organic compound—and those that do not bind the target are removed, usually by affinity chromatography or target capture on paramagnetic beads. The bound sequences are eluted and amplified by PCR to prepare for subsequent rounds of selection in which the stringency of the elution conditions can be increased to identify the tightest-binding sequences.

Sequencing: The initial library was subjected to nine rounds of Melting-Off selection followed by parallel assessment. The SELEX process enriches for sequences over multiple rounds of selection that bind to LPS and remove sequences that respond to components of 1×SELEX buffer or LTA. As a result, the population to be sequenced should contain multiple copies of potential aptamer candidates.

An Illumina (San Diego, CA, US) MiniSee™ system was used to sequence the aptamer libraries after the post-parallel selection using a single-end read technique. Deep sequencing and subsequent data analysis simplifies the traditional approach of performing a large number of screening rounds (Schütze et al., 2011). Numerous sequences were analyzed from the parallel-exposed final libraries. From these sets of data, the library sequence families were constructed at 90% homology (sequence similarity considering mutations, deletions, and insertions).

Bioinformatics and Aptamer Candidate Selection: An individual sequence's frequency in the positive target population was factored in, but the degree of variation between similar sequences was also important, with 90% homology being the minimum requirement (100% match over the entire sequence is not necessary to join a family; up to 2 bases can be mismatched, inserted, or deleted).

One factor is the presence of a sequence in the non-positive-target-exposed populations. Four libraries were collected for sequencing: the post-parallel assessment library that had been recovered from incubation with a positive target in 1×SELEX buffer; post-parallel assessment library recovered after incubation with LTA in 1×SELEX buffer; post-parallel assessment library recovered after incubation with 1×SELEX buffer only; and the parallel assessment library recovered from incubation with LPS in 1×SELEX buffer. The positive population was compared against the counter population to identify sequences that were not removed during the counter selection steps, but which still had affinity for both LTA and LPS. A candidate's rate of enrichment was also considered (see, e.g., Wang et al., 2014). 200 candidates were chosen for microarray synthesis and high throughput assessment.

From these 200 aptamer candidates, SEQ ID NOs:1-5 were specifically identified as examples of the selection process (FIG. 1). The most prevalent family in the population is also highly present in the counter population. However, this sequence (and similar sequences) appeared at high enough frequencies in the positive populations to be still worth investigating in a high-throughput analysis. SEQ ID NOs: 1-5 were selected on the basis of greater proportional representation in the positive population over the counter population and/or negative population.

Finally, all candidate sequences exhibited sufficient stability based upon mfold secondary structure prediction to be considered candidates (FIG. 1).

Microarray Synthesis and Semi-Quantitative Assessment

Microarray Methods: A Cy5-labeled reporter oligonucleotide complimentary to a constant region of the library (5'-GTC GTC CCG AGA GCC TCG/3Cy5Sp/-3' (SEQ ID NO:24)) was synthesized. SEQ ID NO:24 would be displaced during target binding. Oligonucleotides underwent desalting purification.

Data analysis was conducted as follows. The mean background fluorescence value was subtracted from the mean fluorescence value of each candidate prior to the addition of sample as well as each candidate after the addition of sample.

Microarray Results: Candidates were first tested against 100 ng/mL target LPS sample. The result of blocking candidates with Reporter oligonucleotide was imaged. Based upon the image, most candidates interacted well with the Reporter. After this reading was taken, candidates were incubated with target sample overnight at 23° C. The solution at the inlet of the peristaltic pump was then replaced with 1×SELEX buffer to displace the target sample in the microarray.

The same processes were used to analyze candidate response to 1 µg/mL of counter target LPS sample, of which the second run data is presented.

Candidate percent responses to target sample and counter target sample were calculated as the mean of 18 replicate positions. The percent responses themselves were compared to determine candidates that specifically responded to the target. Candidates were ranked according to the ratio of signal loss to the target condition against the signal loss to the counter condition. The greater this score, the more response to the target condition relative to the response to the counter condition. The aptamer candidates with the top five scores (SEQ ID NOs.: 6-10) were then synthesized for qualitative assessment.

Monoclonal Synthesis and Qualitative Validation

Assessment Methods: SEQ ID NOs.: 6-10 were synthesized and purified by desalting. Assessment followed a method similar to that used in the previously described SELEX.

Assessment Results: Initial assessment was carried out with SEQ ID NOs.: 6-10 against just target LPS in 1×SELEX Buffer to determine which candidates demonstrated noticeable response. Differences in the intensity of material present in the candidate lanes represented different amounts of candidate released from magnetic beads as a result of incubation with, and binding to, target LPS. Based upon these results, candidates SEQ ID NO:7 and SEQ ID NO:9 were selected for additional assessment against counter-target LTA.

The chosen candidates were re-assessed against both target and counter-target in the presence of patient samples. SEQ ID NO:9 showed stronger response to target over counter-target.

Example II

An aptamer comprising a core sequence selected from the group consisting of SEQ ID NOs: 11-21 is appropriately labeled with quenching labels and used in an assay to detect LPS in a medical sample taken from a patient (e.g., peritoneal dialysis fluid). The assay is thus used to detect the presence of Gram negative bacteria in the medical sample so as to diagnose an infection in the subject for treatment with an appropriate antibiotic.

REFERENCES (the contents of the entirety of each of which is incorporated herein by this reference):

Ellington and Szostak "In vitro selection of RNA molecules that bind specific ligands." Nature 1990, 346, 818.

Gold et al. "Aptamers and the RNA world, past and present." Cold Spring Harb. Perspect. Biol. 2012, 4, a003582.

Schütze et al. "Probing the SELEX Process with Next-Generation Sequencing." PLoS ONE 6(12): e29604 (2011). DOI: 10.1371/journal.pone.0029604.

Tuerk et al. "Systematic evolution of ligands by exponential enrichment: RNA ligands to bacteriophage t4 DNA polymerase." Science 1990, 249, 505-510.

Wang et al. "Particle Display: A Quantitative Screening Method for Generating High-Affinity Aptamers." Angewandte Communications International Edition 53: 4796-4801 (2014). DOI: 10.1002/anie.201309334.

Zhuo et al. "Recent Advances in SELEX Technology and Aptamer Applications in Biomedicine." *Int. J. Mol. Sci.* 2017, 18, 2142; doi:10.3390/ijms18102142.

M. Zuker "Mfold web server for nucleic acid folding and hybridization prediction." Nucleic Acids Res. 31(13): 3406-3415 (2003). http://mfold.rna.albany.edu/?q=DINAMelt/Quickfold.

US Patent Application Publication 20200249228 A1 to Jiang et al. (Aug. 6, 2020) for "Rapid Diagnosis of Peritonitis in Peritoneal Dialysis Patients."

What is claimed is:

1. A DNA aptamer comprising a polynucleotide comprising a polynucleotide comprising a core sequence set forth in any one of SEQ ID NOS: 11-21.

2. The DNA aptamer of claim 1, wherein the aptamer has a loop structure.

3. The DNA aptamer of claim 1, wherein the aptamer has a double-stranded stem structure.

4. The DNA aptamer of claim 1, further comprising at least one labeling substance.

5. The DNA aptamer of claim 4, wherein the labeling substance is an optical label, an electrochemical label, a radioisotope, or a combination thereof.

6. The DNA aptamer of claim 1, wherein the DNA aptamer has the core sequence of SEQ ID NO: 11.

7. The DNA aptamer of claim 1, wherein the DNA aptamer has the core sequence of SEQ ID NO: 12.

8. The DNA aptamer of claim 1, wherein the DNA aptamer has the core sequence of SEQ ID NO: 13.

9. The DNA aptamer of claim 1, wherein the DNA aptamer has the core sequence of SEQ ID NO: 14.

10. The DNA aptamer of claim 1, wherein the DNA aptamer has the core sequence of SEQ ID NO: 15.

11. The DNA aptamer of claim 1, wherein the DNA aptamer has the core sequence of SEQ ID NO: 16.

12. The DNA aptamer of claim 1, wherein the DNA aptamer has the core sequence of SEQ ID NO: 17.

13. The DNA aptamer of claim 1, wherein the DNA aptamer has the core sequence of SEQ ID NO: 18.

14. The DNA aptamer of claim 1, wherein the DNA aptamer has the core sequence of SEQ ID NO: 19.

15. The DNA aptamer of claim 1, wherein the DNA aptamer has the core sequence of SEQ ID NO: 20.

16. The DNA aptamer of claim 1, wherein the DNA aptamer has the core sequence of SEQ ID NO: 21.

17. The DNA aptamer of claim 1, further comprising: SEQ ID NO:22 and/or SEQ ID NO:23.

18. A biosensor for detecting a Gram-negative bacteria, the biosensor comprising:

the DNA aptamer of claim 1, and a substrate to which the DNA aptamer is fixed.

19. The biosensor of claim 18, further comprising:

a linker between the substrate and the DNA aptamer.

20. A method of detecting lipopolysaccharides ("LPS") in a sample, the method comprising:

utilizing the DNA aptamer of claim 1 to detect the LPS in the sample.

21. A DNA aptamer comprising:

any one of SEQ ID NOs: 6-10; or a polynucleotide that differs from any one of SEQ ID NOs: 6-10 by no more than two purine-to-purine or pyrimidine-to-pyrimidine substitutions and is capable of binding to lipopolysaccharide (LPS).

22. The DNA aptamer of claim 21, wherein the DNA aptamer comprises SEQ ID NO: 7 or SEQ ID NO: 9.

*     *     *     *     *

SEQUENCE LISTING

<160> NUMBER OF SEQ ID NOS: 24

<210> SEQ ID NO 1
<211> LENGTH: 73
<212> TYPE: DNA
<213> ORGANISM: Artificial Sequence
<220> FEATURE:
<223> OTHER INFORMATION: Exemplary DNA Aptamer 1

<400> SEQUENCE: 1
cgaggctctc gggacgactt tagtctgacc aaaaaccaaa accataaagt cgtcccgcct    60
ttaggattta cag                                                      73

<210> SEQ ID NO 2
<211> LENGTH: 73
<212> TYPE: DNA
<213> ORGANISM: Artificial Sequence -continued
<220> FEATURE:
<223> OTHER INFORMATION: Exemplary DNA Aptamer 2

<400> SEQUENCE: 2
cgaggctctc gggacgacct gtcgtcacga aaaactaaaa ccctaagggt cgtcccgcct       60
ttaggattta cag                                                          73

<210> SEQ ID NO 3
<211> LENGTH: 73
<212> TYPE: DNA
<213> ORGANISM: Artificial Sequence
<220> FEATURE:
<223> OTHER INFORMATION: Exemplary DNA APtamer 3

<400> SEQUENCE: 3
cgaggctctc gggacgacga agtcgccacg taaaccgacg accgtcaggt cgtcccgcct       60
ttaggattta cag                                                          73

<210> SEQ ID NO 4
<211> LENGTH: 73
<212> TYPE: DNA
<213> ORGANISM: Artificial Sequence
<220> FEATURE:
<223> OTHER INFORMATION: Exemplary DNA Aptamer 4

<400> SEQUENCE: 4
cgaggctctc gggacgacaa aggagtcacg aaaacaaaaa agagtaaagt cgtcccgcct       60
ttaggattta cag                                                          73

<210> SEQ ID NO 5
<211> LENGTH: 73
<212> TYPE: DNA
<213> ORGANISM: Artificial Sequence
<220> FEATURE:
<223> OTHER INFORMATION: Exemplary DNA Aptamer 5

<400> SEQUENCE: 5
cgaggctctc gggacgacta agtcgtcacg aaagacgtaa aaacgaaagt cgtcccgcct       60
ttaggattta cag                                                          73

<210> SEQ ID NO 6
<211> LENGTH: 72
<212> TYPE: DNA
<213> ORGANISM: Artificial Sequence
<220> FEATURE:
<223> OTHER INFORMATION: Exemplary DNA Aptamer 6

<400> SEQUENCE: 6
cgaggctctc gggacgacct gtcgtcacga aaaacgaaac cctaagggtc gtcccgcctt       60
taggatttac ag                                                           72

<210> SEQ ID NO 7
<211> LENGTH: 73
<212> TYPE: DNA
<213> ORGANISM: Artificial Sequence
<220> FEATURE:
<223> OTHER INFORMATION: Exemplary DNA Aptamer 7

<400> SEQUENCE: 7
cgaggctctc gggacgacct cgtcgcccca aaagataagg atccgaaagt cgtcccgcct       60
ttaggattta cag                                                          73

<210> SEQ ID NO 8
<211> LENGTH: 73
<212> TYPE: DNA
<213> ORGANISM: Artificial Sequence
<220> FEATURE:
<223> OTHER INFORMATION: Exemplary DNA Aptamer 8

<400> SEQUENCE: 8
cgaggctctc gggacgactg tcgcatacac gacagccggc acggaagtgt cgtcccgcct      60
ttaggattta cag                                                        73

<210> SEQ ID NO 9
<211> LENGTH: 73
<212> TYPE: DNA
<213> ORGANISM: Artificial Sequence
<220> FEATURE:
<223> OTHER INFORMATION: Exemplary DNA Aptamer 9

<400> SEQUENCE: 9
cgaggctctc gggacgacat ctacgtcgtc acgggactaa aacctaaagt cgtcccgcct      60
ttaggattta cag                                                        73

<210> SEQ ID NO 10
<211> LENGTH: 73
<212> TYPE: DNA
<213> ORGANISM: Artificial Sequence
<220> FEATURE:
<223> OTHER INFORMATION: Exemplary DNA Aptamer 10

<400> SEQUENCE: 10
cgaggctctc gggacgacgt gagtcgaaga agcacggccg ccccaagggt cgtcccgcct      60
ttaggattta cag                                                        73

<210> SEQ ID NO 11
<211> LENGTH: 30
<212> TYPE: DNA
<213> ORGANISM: Artificial Sequence
<220> FEATURE:
<223> OTHER INFORMATION: Core Sequence 1

<400> SEQUENCE: 11
tttagtctga ccaaaaacca aaaccataaa                                      30

<210> SEQ ID NO 12
<211> LENGTH: 30
<212> TYPE: DNA
<213> ORGANISM: Artificial Sequence
<220> FEATURE:
<223> OTHER INFORMATION: Core Sequence 2

<400> SEQUENCE: 12
ctgtcgtcac gaaaaactaa aaccctaagg                                      30

<210> SEQ ID NO 13
<211> LENGTH: 30
<212> TYPE: DNA
<213> ORGANISM: Artificial Sequence
<220> FEATURE:
<223> OTHER INFORMATION: Core Sequence 3

<400> SEQUENCE: 13
gaagtcgcca cgtaaaccga cgaccgtcag                                      30

<210> SEQ ID NO 14
<211> LENGTH: 30
<212> TYPE: DNA
<213> ORGANISM: Artificial Sequence
<220> FEATURE:
<223> OTHER INFORMATION: Core Sequence 4

<400> SEQUENCE: 14
aaaggagtca cgaaaacaaa aaagagtaaa                                    30

<210> SEQ ID NO 15
<211> LENGTH: 30
<212> TYPE: DNA
<213> ORGANISM: Artificial Sequence
<220> FEATURE:
<223> OTHER INFORMATION: Core Sequence 5

<400> SEQUENCE: 15
taagtcgtca cgaaagacgt aaaaacgaaa                                    30

<210> SEQ ID NO 16
<211> LENGTH: 29
<212> TYPE: DNA
<213> ORGANISM: Artificial Sequence
<220> FEATURE:
<223> OTHER INFORMATION: Core Sequence 6

<400> SEQUENCE: 16
ctgtcgtcac gaaaaacgaa accctaagg                                     29

<210> SEQ ID NO 17
<211> LENGTH: 30
<212> TYPE: DNA
<213> ORGANISM: Artificial Sequence
<220> FEATURE:
<223> OTHER INFORMATION: Core Sequence 7

<400> SEQUENCE: 17
ctcgtcgccc caaaagataa ggatccgaaa                                    30

<210> SEQ ID NO 18
<211> LENGTH: 30
<212> TYPE: DNA
<213> ORGANISM: Artificial Sequence
<220> FEATURE:
<223> OTHER INFORMATION: Core Sequence 8

<400> SEQUENCE: 18
tgtcgcatac acgacagccg gcacggaagt                                    30

<210> SEQ ID NO 19
<211> LENGTH: 30
<212> TYPE: DNA
<213> ORGANISM: Artificial Sequence
<220> FEATURE:
<223> OTHER INFORMATION: Core Sequence 9

<400> SEQUENCE: 19
atctacgtcg tcacgggact aaaacctaaa                                    30

<210> SEQ ID NO 20
<211> LENGTH: 30
<212> TYPE: DNA
<213> ORGANISM: Artificial Sequence
<220> FEATURE:
<223> OTHER INFORMATION: Core Sequence 10

<400> SEQUENCE: 20
gtgagtcgaa gaagcacggc cgccccaagg                                    30

<210> SEQ ID NO 21
<211> LENGTH: 27
<212> TYPE: DNA
<213> ORGANISM: Artificial Sequence
<220> FEATURE:
<223> OTHER INFORMATION: DNA Aptamer Core Sequence
<220> FEATURE:
<221> NAME/KEY: R
<222> LOCATION: (13)..(13)
<223> OTHER INFORMATION: A or G
<220> FEATURE:
<221> NAME/KEY: V
<222> LOCATION: (14)..(14)
<223> OTHER INFORMATION: A, C, or G
<220> FEATURE:
<221> NAME/KEY: H
<222> LOCATION: (15)..(15)
<223> OTHER INFORMATION: A, C, or T
<220> FEATURE:
<221> NAME/KEY: V
<222> LOCATION: (16)..(16)
<223> OTHER INFORMATION: A, C, or G
<220> FEATURE:
<221> NAME/KEY: V
<222> LOCATION: (21)..(21)
<223> OTHER INFORMATION: A, C, or G
<220> FEATURE:
<221> NAME/KEY: M
<222> LOCATION: (22)..(22)
<223> OTHER INFORMATION: A or C
<220> FEATURE:
<221> NAME/KEY: B
<222> LOCATION: (23)..(24)
<223> OTHER INFORMATION: C, G, or T

<400> SEQUENCE: 21
gtcgtcacga aarvhvaaaa vmbbaaa                                        27

<210> SEQ ID NO 22
<211> LENGTH: 18
<212> TYPE: DNA
<213> ORGANISM: Artificial Sequence
<220> FEATURE:
<223> OTHER INFORMATION: Primer Annealing Region

<400> SEQUENCE: 22
cgaggctctc gggacgac                                                 18

<210> SEQ ID NO 23
<211> LENGTH: 25
<212> TYPE: DNA
<213> ORGANISM: Artificial Sequence
<220> FEATURE:
<223> OTHER INFORMATION: Primer Annealing Region

<400> SEQUENCE: 23
gtcgtcccgc ctttaggatt tacag                                         25

<210> SEQ ID NO 24
<211> LENGTH: 19
<212> TYPE: DNA
<213> ORGANISM: Artificial Sequence
<220> FEATURE:
<223> OTHER INFORMATION: Reporter
<220> FEATURE:
<221> NAME/KEY: N
<222> LOCATION: (19)..(19)
<223> OTHER INFORMATION: 3Cy5Sp -continued

```
<220> FEATURE:
<221> NAME/KEY: misc_feature
<222> LOCATION: (19)..(19)
<223> OTHER INFORMATION: n is a, c, g, or t

<400> SEQUENCE: 24
gtcgtcccga gagcctcgn                                                    19
```